US012630585B2

(12) United States Patent
Seyedsayamdost et al.

(10) Patent No.: US 12,630,585 B2
(45) Date of Patent: May 19, 2026

(54) ANTIBACTERIAL TRYGLYSIN AGENTS

(71) Applicants: The Trustees of Princeton University, Princeton, NJ (US); THE BOARD OF TRUSTEES OF THE UNIVERSITY OF ILLINOIS, a body corporate politic the State of Illinois, Urbana, IL (US)

(72) Inventors: Mohammad R. Seyedsayamdost, Princeton, NJ (US); Michael J. Federle, La Grange, IL (US); Brett C. Covington, New Brunswick, NJ (US); Leah B. Bushin, San Diego, CA (US); Britta E. Rued, Chicago, IL (US); John Ambrose, Princeton, NJ (US)

(73) Assignees: THE TRUSTEES OF PRINCETON UNIVERSITY, Princeton, NJ (US); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 524 days.

(21) Appl. No.: 18/266,325

(22) PCT Filed: Dec. 8, 2021

(86) PCT No.: PCT/US2021/062338

§ 371 (c)(1),
(2) Date: Jun. 9, 2023

(87) PCT Pub. No.: WO2022/125620

PCT Pub. Date: Jun. 16, 2022

(65) Prior Publication Data

US 2024/0051995 A1 Feb. 15, 2024

Related U.S. Application Data

(60) Provisional application No. 63/123,270, filed on Dec. 9, 2020.

(51) Int. Cl.

| | |
|---|---|
| ***C07K 7/06*** | (2006.01) |
| ***A61P 31/04*** | (2006.01) |
| ***C07K 1/16*** | (2006.01) |
| ***C12N 1/205*** | (2026.01) |

(52) U.S. Cl.

CPC ................ *C07K 7/06* (2013.01); *A61P 31/04* (2018.01); *C07K 1/16* (2013.01); *C12N 1/205* (2021.05); *C12N 2500/22* (2013.01)

(58) Field of Classification Search

None

See application file for complete search history.

(56) References Cited

PUBLICATIONS

European Search Report corresponding EP Application No. 21904307.2, dated Oct. 18, 2024.

Caruso et al., "Radical Approach to Enzymatic [beta]—Thioether Bond Formation", Journal of the American Chemical Society, vol. 141, No. 2, pp. 990-997, Dec. 6, 2018.

Schramma et al., "Lysine-Tryptophan-Crosslinked Peptides Produced by Radical SAM Enzymes in Pathogenic *Streptococci*", ACS Chemical Biology, vol. 12, No. 4, pp. 922-927, Apr. 21, 2017.

Clark et al., "RaS-RiPPs in 1-15 *Streptococci* and the Human Microbiome", ACS Bio & Med Chem Au, vol. 2, No. 4, pp. 328-339, Mar. 21, 2022.

Caruso et al., "Radical SAM Enzyme 1-15 QmpB Installs Two 9-Membered Ring Sactionine Macrocycles during Biogenesis of a Ribosomal Peptide Natural Product", The Journal of Organic Chemistry, vol. 86, No. 16, pp. 11284-11289, Aug. 5, 2021.

International Search Report and Written Opinion for corresponding PCT Application No. PCT/US2021/062338, dated Mar. 16, 2022.

Bushin et al., "Charting an Unexplored Streptococcal Biosynthetic Landscape Reveals a Unique Peptide Cyclization Motif", J. Am. Chern. Soc., vol. 40, pp. 17674-17684, Nov. 6, 2018.

Bushin et al., "Discovery and Biosynthesis of Streptosactin, a Sactipeptide with an Alternative Topology Encoded by Commensal Bacteria in the Human Microbiome", J. Am. Chern. Soc., vol. 142, pp. 16265-16275, Aug. 26, 2020.

Ihara et al., "Purification, Characterization, and Molecular Cloning of Lactonizing Lipase from Pseudomonas Species", The Journal of Biological Chemistry, vol. 266, No. 27, pp. 18135-18140, Sep. 26, 1991.

Rued et al., "Quorum Sensing in *Streptococcus mutans* Regulates Production of Tryglysin, a Novel RaS-RiPP Antimicrobial Compound", mBio, vol. 12, Issue 2, Mar. /Apr. 2021.

*Primary Examiner* — Kevin S Orwig

(74) *Attorney, Agent, or Firm* — Meagher Emanuel Laks Goldberg & Liao LLP

(57) ABSTRACT

There is currently a high demand for new therapeutic antibiotics with new mechanisms of action. Disclosed are two small molecules, tryglysin A and B, with novel chemical structures and potent antibiotic activity against a narrow spectrum of bacteria. This narrow spectrum of activity indicates the tryglysins could be working through a novel antibiotic mechanism of action. Due to this narrow spectrum, the tryglysins could be used as highly targeted therapeutics to treat or prevent disease without disturbing other important, "beneficial" bacteria within the human microbiome, which is a great improvement over virtually all other clinically used antibiotics that are broad-spectrum. The tryglysins are potent against several streptococcal pathogens, including *Streptococcus pneumonia*, the leading cause of pneumonia, and *Streptococcus mutans*, the primary causative agent of tooth decay and gum disease. The tryglycins may allow the development of therapeutics for the treatment and/or prevention of disease caused by these streptococci.

9 Claims, 4 Drawing Sheets

Specification includes a Sequence Listing.

ANTIBACTERIAL TRYGLYSIN AGENTS

CROSS-REFERENCE TO RELATED APPLICATIONS

This application claims priority to U.S. Provisional Patent Application No. 63/123,270 filed Dec. 9, 2020, which is hereby incorporated in its entirety by reference.

STATEMENT REGARDING FEDERALLY SPONSORED RESEARCH OR DEVELOPMENT

The invention was made with government support under Grant Nos. AI124786 and AI091779 awarded by the National Institutes of Health and CHE1847932 awarded by the National Science Foundation. The government has certain rights in the invention.

SEQUENCE LISTING

A copy of the sequence listing is submitted concurrently with the specification electronically via EFS-Web as an ASCII formatted sequence listing with a file name of "PRIN78876Sequence.txt", created on Dec. 1, 2021, and having a size of 1,848 bytes. The sequence listing contained in this ASCII formatted document is part of the specification and is herein incorporated by reference in its entirety.

TECHNICAL FIELD

The present disclosure relates to antibiotics with new mechanisms of action, and specifically to small molecules with novel chemical structures and potent antibiotic activity against a narrow spectrum of bacteria.

BACKGROUND

In bacteria, quorum sensing (QS) coordinates a myriad of biological processes that include natural competence, sporulation, biofilm formation, and niche adaptation during host colonization in symbiotic and pathogenic interactions. Bacteria often use complex regulatory systems to sense and respond to QS signals termed 'autoinducers' or 'pheromones'. The chemical composition of autoinducers varies among species, but best-characterized are the signals of Gram-negative and Gram-positive bacteria that utilize acyl-homoserine lactones and oligopeptides, respectively.

In recent years a class of transcriptional regulators that respond to peptide-based QS signals has emerged as important regulatory factors in Gram-positive species: the RRNPP (Rap/Rgg/NprR/PlcR/PrgX) family. Among members of this family, the Rgg regulators are the most common subclass encoded in streptococci, and several occurrences of Rgg paralogs are frequently observed within any given genome. Rgg regulators sense and respond to SHPs (Short Hydrophobic Peptides) by directly binding these linear peptides, which induce allosteric changes in Rgg transcriptional activity. Rgg proteins have been characterized in various streptococcal species, including the medically relevant *Streptococcus pyogenes, Streptococcus pneumoniae*, and *Streptococcus mutans*. Multiple studies demonstrate their involvement in processes such as virulence gene regulation, biofilm formation, capsule production, resistance to host factors, and competence.

SHP/Rgg systems are frequently associated with RaS-RiPP biosynthetic operons in streptococci. RaS (Radical S-adenosyl-L-methonine)-RiPP (Ribosomally synthesized and Post-translationally modified Peptides) operons give rise to peptide secondary metabolites that are modified by one or more RaS enzymes, a large enzyme superfamily characterized by its ability to reductively activate SAM (S-adenosyl-L-methionine) with the aid of an active site-bound [4Fe-4S] cluster. RaS-RiPP operons typically code for a precursor peptide, a RaS enzyme, in some cases an RRE (RiPP Recognition Element) protein, and additional genes for modification and transport. The RaS enzymes in these operons install unprecedented cyclization motifs onto the precursor peptides via a variety of biochemical reactions. But while the reactions carried out by the RaS enzymes in several RaS-RiPP operons have been characterized, the final secondary metabolite is in most cases unknown and the biological relevance of these peptides remains unexplored.

BRIEF SUMMARY

The present disclosure is drawn to uses for several such unknown secondary metabolites, given the name tryglysins, and in particular macrocyclic compounds of formula (I) or analogs or derivatives thereof:

(I)

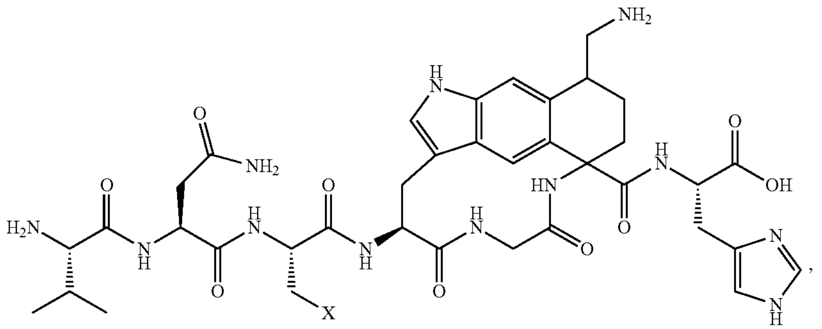

where X is OH or SH.

A first aspect of the present disclosure is drawn to compositions comprising a tryglysin, wherein the tryglysin is a macrocyclic compound of formula (I) or an analog or derivative thereof as described above, for use in a method of treating an infection by at least one streptococcal pathogen (such as one or more strains of *S. ferus, S. mitis, S. mutans, S. oralis*, or *S. pneumonia*). In some embodiments, the composition may be an antibiotic preparation; that is, the composition may comprise the tryglysin, and a pharmaceutically acceptable carrier. In some embodiments, the composition may be a mouth wash, oral rinse, or toothpaste; that is, the composition may comprise the tryglysin, less than about 20% by weight of an alcohol, and a flavoring agent, an abrasive agent, or both.

A second aspect of the present disclosure is drawn to a method for treatment or prevention of a disease in a patient caused by at least one streptococcal pathogen (such as one or more strains of *S. ferus, S. mitis, S. mutans, S. oralis*, or *S. pneumonia*). The method comprises administering to a patient in need of such treatment or prevention an effective amount of a tryglysin, wherein the tryglysin is a macrocyclic compound of formula (I) or an analog or derivative thereof as described above. In some embodiments, the concentration of the tryglysin may be between 10 nM and 500 nM. In some embodiments, the minimal inhibitory concentration (MIC) of the tryglysin may be <100 nM. In some embodiments, an inhibitory effect of the tryglysin may be specific to the at least one streptococcal pathogen.

A third aspect of the present disclosure is drawn to a recombinant microorganism. The microorganism comprises (i) one or more genes configured to express WgkA fused to a purification tag, WgkB, and WgkC, (ii) one or more genes configured to express site-directed mutants of WgkA fused to a purification tag, variants of WgkB, and variants of WgkC to make a tryglysin derivative that contain a canonical amino acid at residues 1, 2, 3, 5, and 7, from the N-terminus of the tryglysin derivate, of tryglysin with either lysine, arginine, isoleucine, or leucine at residue 6, or (iii) a combination thereof. In some embodiments, the one or more genes configured to express WgkA fused to a purification tag comprises *S. ferus* wgkA or *S. mutans* wgkA. In some embodiments, the recombinant microorganism is a strain of *E. coli*.

A fourth aspect of the present disclosure is drawn to a method for producing a tryglysin using the endogenous producing host such as *Streptococcus ferus*. Upon growth of the host, such as *Streptococcus ferus*, tryglysin is isolated using a simplified and rapid two-column procedure, consisting of graphite-based solid-phase extraction (SPE) followed by performance liquid chromatography (HPLC) separation.

DETAILED DESCRIPTION

Figure 1:
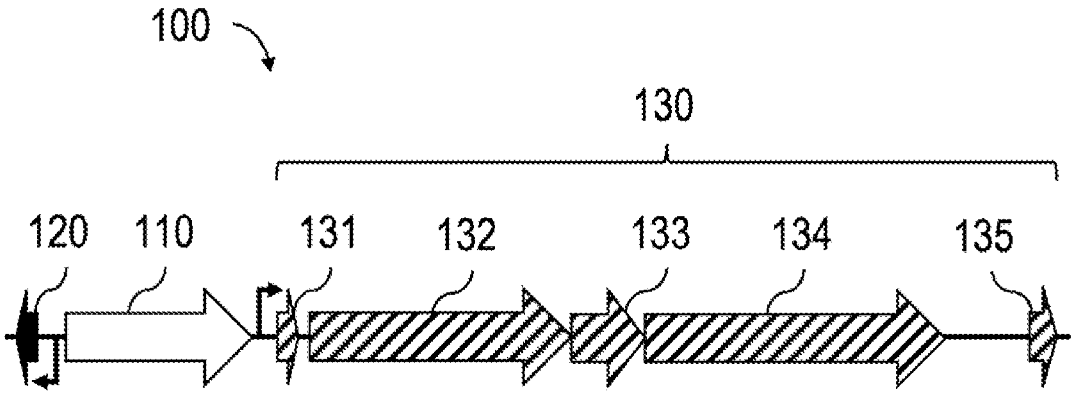
FIG. 1 is schematic of an SHP/Rgg signaling system paired to an operon producing a RaS-RiPP in a strain of *S. mutans*.

Disclosed are compositions comprising a tryglysin, and specifically where the tryglysin is a macrocyclic compound of formula (I) or an analog or derivative thereof:

(I)

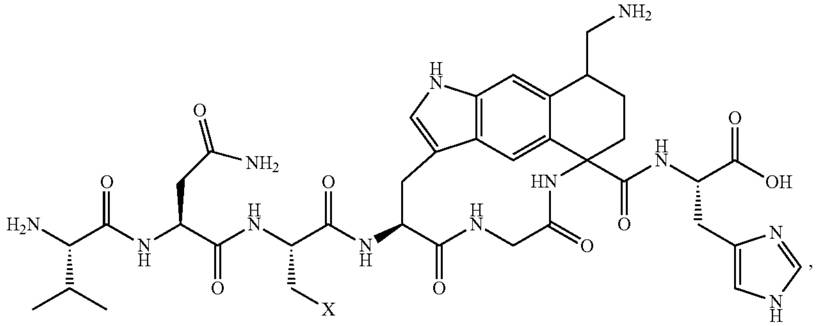

where X is OH or SH. When X is OH, the tryglysin may be referred to as "Tryglysin A", and when X is SH, the tryglysin may be referred to as "Tryglysin B". As can be seen, these may be 7-mer macrocyclic peptides consisting of the sequence VNSWGKH (SEQ ID NO:1) (Tryglysin A) or VNCWGKH (SEQ ID NO:2) (Tryglysin B) and carrying the tetrahydro[5,6]benzindole modification.

The term "analog" as used herein includes parts, extensions, substitutions, variants, modifications or chemical equivalents and derivatives thereof of the compound of formula (I) that perform substantially the same function as the compound of formula (I) in substantially the same way.

The term "derivative" as used herein refers to any physiologically tolerated derivative of a compound of the formula (I), for example an N-oxide, which on administration to a mammal such as, for example, a human is able to form (directly or indirectly) a compound of the formula (I) or an active metabolite thereof.

Such compositions may be used for treating bacterial infections, and specifically treating infections caused by at least one streptococcal pathogen. In some embodiments, the at least one streptococcal pathogen may be one or more strains of *Streptococcus acidominimus, Streptococcus agalactiae, Streptococcus anginosus, Streptococcus bovis, Streptococcus cricetus, Streptococcus cristatus, Streptococcus downei, Streptococcus dysgalactiae, Streptococcus equi subsp. equi, Streptococcus ferus, Streptococcus gordonii,*

*Streptococcus macacae, Streptococcus mitis, Streptococcus mutans, Streptococcus oralis, Streptococcus parasanguinis, Streptococcus pneumoniae, Streptococcus pyogenes, Streptococcus ratti, Streptococcus salivarius, Streptococcus salivarius subsp. thermophilus, Streptococcus sanguinis, Streptococcus sobrinus, Streptococcus suis, Streptococcus uberis*, or *Streptococcus vestibularis*. In some embodiments, the at least one streptococcal pathogen may be a strain of *Streptococcus ferus, Streptococcus mitis, Streptococcus mutans, Streptococcus oralis*, or *Streptococcus pneumonia*. In some embodiments, the at least one streptococcal pathogen may be a strain of *Streptococcus ferus*. In some embodiments, the at least one streptococcal pathogen may be a strain of *Streptococcus mitis*. In some embodiments, the at least one streptococcal pathogen may be a strain of *Streptococcus mutans*. In some embodiments, the at least one streptococcal pathogen may be a strain of *Streptococcus oralis*. In some embodiments, the at least one streptococcal pathogen may be a strain of *Streptococcus pneumonia*.

In some embodiments, the streptococcal pathogen may belong to the *viridans* group. In some embodiments, the streptococcal pathogen may belong to a subgroup of the *viridans* group, such as the *mutans* group, *mitis* group, *salivarius* group, *sanguinis* group, *bovis* group, or *anginosus* group. In some embodiments, the streptococcal pathogen may belong to the *mutans* group. In some embodiments, the streptococcal pathogen may belong to the *mitis* group. In some embodiments, the streptococcal pathogen may belong to the *salivarius* group. In some embodiments, the streptococcal pathogen may belong to the *sanguinis* group. In some embodiments, the streptococcal pathogen may belong to the *bovis* group. In some embodiments, the streptococcal pathogen may belong to the *anginosus* group.

In some embodiments, the composition may be a pharmaceutical or antibiotic preparation comprising the tryglysin and a pharmaceutically acceptable carrier.

As used herein, "pharmaceutically acceptable carrier" means any and all solvents, dispersion media, coatings, antibacterial and antifungal agents, isotonic and absorption delaying agents, and the like that are physiologically compatible. Some examples of pharmaceutically acceptable carriers merely by way of illustration, are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

The pharmaceutical or antibiotic preparation may be in a variety of forms, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and prophylactic or therapeutic application. Typical compositions are in the form of injectable or infusible solutions, such as compositions similar to those used for passive immunization of humans. In some embodiments, the mode of administration is parenteral (e.g., intravenous, subcutaneous, intraperitoneal, intramuscular).

The pharmaceutical or antibiotic preparation is typically sterile and stable under the conditions of manufacture and storage. The composition can be formulated as a solution, microemulsion, dispersion, liposome, or other ordered structure suitable to high drug concentration. Sterile injectable solutions may be prepared by incorporating the composition according to formula (I) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In some embodiments, the composition may be an oral care composition (such as a mouth wash, oral rinse, or toothpaste) comprising (i) the tryglysin, and (ii) at least one additional component. In some embodiments, the at least one additional component is an abrasive agent, a flavoring agent, an alcohol, fluoride, a thickening agent, a humectant, and/or a detergent. In some embodiments, the at least one additional component is abrasive agent, a flavoring agent, an alcohol, or a combination thereof.

The oral care compositions may include an abrasive agent, which may be any orally or cosmetically acceptable abrasive. Suitable abrasives include without limitation, silica, silicate, silicon, alumina (including calcined aluminum oxide), aluminosilicates, such as bentonite, zeolite, kaolin, and mica, siliceous or diatomaceous earth, pumice, calcium carbonate, cuttlebone, insoluble phosphates, composite resins, such as melamine resin, phenolic resin, and urea-formaldehyde resin, polycarbonate, silicon carbide, boron carbide, microcrystalline wax, microcrystalline cellulose, including combinations of colloidal microcrystalline cellulose and carboxymethylcellulose, and combinations and/or derivatives of all of the above. Mica may be sheet mica, scrap mica or flake mica, as exemplified by muscovite, biotite or phlogopite type micas. Among insoluble phosphates useful as abrasives are orthophosphates, polymetaphosphates and pyrophosphates. Illustrative examples are dicalcium orthophosphate dihydrate, dicalcium phosphate dihydrate, calcium hydrogen phosphate, calcium pyrophosphate, P-calcium pyrophosphate, tricalcium phosphate, calcium metaphosphate, potassium metaphosphate, and sodium metaphosphate.

The oral care compositions may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight e.g., about 0.5 to about 1.5% by weight.

The oral care compositions may include edible monohydric alcohols, such as ethanol, and/or edible polyhydric alcohols such as glycerol, sorbitol, xylitol, propylene glycol as well as other polyols and mixtures thereof. In some embodiments, the oral care composition comprises less than 20% by weight of the alcohol(s).

Also disclosed is a method for treatment or prevention of a disease in a patient caused by at least one streptococcal pathogen. The method comprises administering to a patient in need of such treatment or prevention an effective amount of a tryglysin, wherein the tryglysin is a macrocyclic compound of formula (I) or an analog or derivative thereof, where X is OH or SH.

In some embodiments, the at least one streptococcal pathogen may be one or more strains of *Streptococcus acidominimus, Streptococcus agalactiae, Streptococcus anginosus, Streptococcus bovis, Streptococcus cricetus, Streptococcus cristatus, Streptococcus downei, Streptococcus dysgalactiae, Streptococcus equi subsp. equi, Streptococcus ferus, Streptococcus gordonii, Streptococcus macacae, Streptococcus mitis, Streptococcus mutans, Streptococcus oralis, Streptococcus parasanguinis, Streptococcus pneumoniae, Streptococcus ratti, Streptococcus salivarius, Streptococcus salivarius subsp. thermophilus, Streptococcus sanguinis, Streptococcus sobrinus, Streptococcus suis, Streptococcus uberis*, or *Streptococcus vestibularis*. In some embodiments, the at least one streptococcal pathogen may be a strain of *Streptococcus ferus, Streptococcus mitis, Streptococcus mutans, Streptococcus oralis*, or *Streptococcus pneumonia*. In some embodiments, the at least one streptococcal pathogen may be a strain of *Streptococcus ferus*. In some embodiments, the at least one streptococcal pathogen may be a strain of *Streptococcus mitis*. In some embodiments, the at least one streptococcal pathogen may be a strain of *Streptococcus mutans*. In some embodiments, the at least one streptococcal pathogen may be a strain of *Streptococcus oralis*. In some embodiments, the at least one streptococcal pathogen may be a strain of *Streptococcus* pneumonia.

In some embodiments, the streptococcal pathogen may belong to the *viridans* group. In some embodiments, the streptococcal pathogen may belong to a subgroup of the *viridans* group, such as the *mutans* group, *mitis* group, *salivarius* group, *sanguinis* group, *bovis* group, or *anginosus* group. In some embodiments, the streptococcal pathogen may belong to the *mutans* group. In some embodiments, the streptococcal pathogen may belong to the *mitis* group. In some embodiments, the streptococcal pathogen may belong to the *salivarius* group. In some embodiments, the streptococcal pathogen may belong to the *sanguinis* group. In some embodiments, the streptococcal pathogen may belong to the *bovis* group. In some embodiments, the streptococcal pathogen may belong to the *anginosus* group.

In some embodiments, the effective amount is sufficient to result in a concentration of the tryglysin of between and including 10 nM and 500 nM. In some embodiments, the concentration may be between and including 10 nM and 100 nM. In some embodiments, the concentration may be less than or equal to than 1 μM. In some embodiments, the concentration may be less than or equal to 500 nM. In some embodiments, the concentration may be less than or equal to 200 nM. In some embodiments, the concentration may be less than or equal to 100 nM. In some embodiments, the concentration may be less than or equal to 50 nM.

In some embodiments, the minimal inhibitory concentration (MIC) of the tryglysin may be <100 nM.

In some embodiments, the inhibitory effect of the tryglysin may be specific to the at least one streptococcal pathogen. For example, while the tryglsin may be capable of exhibiting complete growth inhibition of strains of *S. mitis* and *S. oralis*, it may have no (or de minimis) inhibitory effect on other microbacteria, such as strains of *L. lactis*.

Also disclosed is a recombinant microorganism, comprising (i) one or more genes configured to express WgkA fused to a purification tag, WgkB, and WgkC, (ii) one or more genes configured to express site-directed mutants of WgkA in which the five residues in the core peptide (i.e., other than lysine or tryptophan, see structure I) are substituted by one of the remaining 19 canonical amino acids, wt WgkB or site-directed mutants that exhibit higher enzymatic activity, and variants of WgkC to make a tryglysin derivative that contain a canonical amino acid at residues 1, 2, 3, 5, and 7, from the N-terminus of the tryglysin derivate, of tryglysin with either lysine, arginine, isoleucine, or leucine at residue 6; or (iii) a combination thereof.

As will be understood by those in the art, the process of forming tryglysin involves the interaction of the expressed WgkA, WgkB, and WgkC (or variants thereof). WgkA is the unmodified peptide, which is then modified by WgkB and WgkC and proteolyzed, and the product is referred to as tryglysin.

In some embodiments, the one or more genes configured to express WgkA fused to a purification tag comprises *S. ferus* wgkA or *S. mutans* wgkA. In some embodiments, the one or more genes configured to express WgkA fused to a purification tag comprises *S. ferus* wgkA or *S. mutans* wgkA. In some embodiments, the one or more genes configured to express WgkA fused to a purification tag comprises *S. ferus* wgkA. In some embodiments, the one or more genes configured to express WgkA fused to a purification tag comprises *S. mutans* wgkA. In some embodiments, the one or more genes configured to express WgkA fused to a purification tag comprises *S. ferus* wgkA and is coexpressed with *S. ferus* WgkB, or a variant thereof, and *S. ferus* WgkC, or a variant thereof. In some embodiments, the one or more genes configured to express WgkA fused to a purification tag comprises S. mutan wgkA and is coexpressed with *S. mutans* WgkB, or a variant thereof, and *S. mutans* WgkC, or a variant thereof In some embodiments, the recombinant microorganism may be a bacterium. In some embodiments, the bacterium may be a gram-negative bacterium. In some embodiment, the gram-negative bacterium may be a strain of *E. coli*.

The wgk operon 130 includes wgkA 131, wgkB 132, wgkC 133, wgkD 134, and SMU_1505c 135. Here, wgkA 131 is a previously unannotated sequence encoding a 21-amino-acid prepeptide (MLTKKEFSVPKTTKVNCWGKH, SEQ ID NO:3), wgkB 132 is a RaS enzyme, wgkC 133 codes for an RRE protein, wgkD 134 is a predicted transporter, and SMU_1505c 135 is a pseudogene with homology to the beta-subunit of phenylalanine-tRNA ligase.

In some strains (such as *S. ferus*), the cysteine residue in wgkA may be replaced by a serine residue at amino acid 17 in the prepeptide, so the prepeptide encoded by wgkA in those strains may be MLTKKEFSVPKTTKVNSWGKH (SEQ ID NO4).

Any appropriate purification tag may be utilized. Such tags may include any other protein or peptide that may be used for purification, detection or any other purpose to remain attached to the expressed protein of interest. Purification tags are well known in the art and include, but are not limited to: polyhistidine tags, polyarginine tags, glutinone-S-transferase (GST), maltose binding protein (MBP), S-tag, influenza virus HA tag, thioredoxin, staphylococcal protein A tag, the FLAG™ epitope, AviTag epitope (for subsequent biotinylation), and the c-myc epitope.

The method may comprise providing a recombinant microorganism as described above. The microorganisms are grown according to known techniques, and allowed to express the WgkA or site-directed mutants of WgkA fused to a purification tag. The microorganisms may be incubated for, e.g., between 12 and 24 hours.

For example, an *E. coli* strain may be grown with a plasmid expressing wgkA with an appropriate purification tag, wgkB, and wgkC. After growth in chemically defined media as known in the art, plus 1% glucose at 37° C. in an atmosphere of 5% $CO_2$, the purification tag is used to purify modified WgkA. For example, when polyhistadine tags are used, it is understood that immobilized metal ion affinity chromatography (IMAC) techniques will be appropriate for purifying the proteins. Then modified WgkA is cleaved with an appropriate protease to deliver the final 7mer product tryglysin. In some embodiments, two or more proteases are used. This process is generally used to cleave the purification tag from the tryglysin. The choice of proteases is generally based on the cleavage tag sequence utilized by the purification tag. For example, when a purification tag contains a HRV 3C Protease cleavage site, an HRV 3C protease can be used to generate a tagless WgkA (for example), and then further cleaving can occur to generate the tryglysin. Other known protease approaches may be appropriate as understood in the art. *E. coli* strains for plasmid construction and propagation may, for example, be derived from *E. coli* BH10c or DH5a. *E. coli* strains were grown on Luria-Bertani (BD Biosciences) plates with 1.4% Bacto agar at 37° C. or in Luria-Bertani (LB) broth or terrific broth with shaking at 200 rpm. When required, spectinomycin (100 mg/ml), erythromycin (0.5 mg/ml for *S. mutans;* 500 mg/ml for *E. coli*), kanamycin (50 to 100 mg/ml), and chloramphenicol (3 mg/ml) were added to *S. mutans* or *E. coli* culture media. Ampicllin (100 mg/ml) was added to *E. coli* cultures when required.

In some embodiments, the recombinant microorganism is from a first species of bacteria (such as *E. coli*), the WgkA is expressed from a gene from a second species of bacteria, the first species being different from the second species.

In some embodiments, a method for producing tryglysin, comprises isolating trylglysin directly from an original host.

The method may include growing a wild-type host encoding a wgk gene cluster, allowing the wild-type host to produce a trylglysin, and isolating the trylglysin directly from the host. In some embodiments, a streptococcal wild-type host is utilized. In some embodiments, the wild-type host is *Streptococcus ferus.*

The tryglysins are very polar compounds and do not retain on traditional solid phase extraction resins or on traditional reverse phase HPLC columns. Thus, further improvements in isolation and purification are useful and desirable. This can be accomplished using porous graphitic carbon or hypercarb resin for the initial step of purification that allows for more selective isolation of the tryglysins from bacterial culture, and implement polar C-18 HPLC columns with high aqueous content mobile phases (>95% water) to retain and purify the polar tryglysins.

In some embodiments, isolating the tryglysin comprises a simplified, two-step procedure in which cell-free supernatants are applied to a manual porous graphitic carbon column (such as a Hypercarb™ column), which is then washed with water to remove impurities. Bound tryglysin is eluted with 50% acetonitrile (in water). This fraction is dried, resuspended in water, and purified to homogeneity on a polar C-18 HPLC column with a high aqueous content mobile phase (such as a Luna Omega Polar HPLC column) that is resolved with an isocratic gradient of 2-4% acetonitrile (in water) with the mobile phase containing 0.1% formic acid. The pure tryglysin fractions are collected, dried, and redissolved to the desired concentration for downstream experiments.

Additionally, the yield of tryglysin can be quite low. In some embodiments of a method for eliciting tryglysins (either separate from or in addition to the method for isolating trygylsin described above), a material comprising zinc is added to the bacterial culture in order to increase production of the tryglysins. In some embodiments, the material comprising zinc may be a zinc salt. In some embodiment, the zinc salt is zinc chloride ($ZnCl_2$). In some embodiments, the material comprising zinc is added at concentrations between 0.5 and 50 μM. In some embodiments, the concentration is between 0.5 and 5 μM. in some embodiments, the concentration is between 0.5 and 2 μM. In some embodiments, the target concentration of the material comprising zinc is between 1 μM. In some embodiments, some or all of the material comprising zinc is added prior to growing the host culture. In some embodiments, all of the material comprising zinc is introduced to the growth medium used to grow the host culture. The increase in tryglysin production can be significant. In one example, by adding 1 μM of $ZnCl_2$ to a *S. ferus* culture, a 50% increase in tryglysin production was experienced.

Example 1—Preparation of Tryglysin A

The synthetic 7-mer peptide containing the appropriate modification was prepared using a construct in which *S. ferus* wgkA carrying an N-terminal purification tag, wgkB, and wgkC were coexpressed from the same plasmid in *Escherichia coli.*

The following plasmids were obtained via transformation of the final construct into chemically competent *E. coli* DH5a cells via heat shock. All PCR products were purified using the Qiagen PCR purification kit (Fisher Scientific). The Qiagen Gel Extraction kit (Thermo-Fisher) was used to purify DNA fragments and plasmids following digestion with restriction enzymes. Prior to ligation or Gibson Assembly, all linearized vectors were treated with recombinant shrimp alkaline phosphatase (rSAP) (NEB). All ligation reactions were performed with T4 DNA Ligase (NEB), and all DNA assemblies were performed with Gibson Assembly Master Mix (NEB). All cloning reagents were used according to instructions. Assembled plasmids were confirmed by Sanger sequencing. Plasmids were constructed as follows.

To obtain pRSFDuet-1_6HMBP, pBAD6HMBPP_HISTFLAG was purified using a Qiagen Gel Extraction kit (Thermo-Fisher) according to the manufacturer's instructions and digested with restriction enzymes NcoI and BamHI (NEB) to yield a DNA fragment encoding a 6xHis-MBP tag containing a polylinker and HRV-3C protease cleavage site. The fragment was then inserted by ligation into NcoI/BamHI-digested pRSFDuet-1.

To obtain pRSFDuet-1_6HMBPwgkA_wgkBC_DSM20646, a DNA fragment containing wgkA and appropriate overlap regions was PCR amplified with primers wgkA_DSM20646_F (AGTTCTGTTTCAGGGTCC GGAATTCGGATCCATGT CACCTAAAAAAGAGTTTA ATGCTCC, SEQ ID NO:5)/ wgkA_DSM20646_R (ATGCGGCCGCAAGCTTG TCGACCTGCAGTTAATG CTTACCCCAACTATTAAC TTTAGTTG, SEQ ID NO:6) from *Streptococcus ferus* DSM20646 genomic DNA that was isolated using the Wizard Genomic purification kit (Promega). A wgkBC DNA fragment was generated in the same way, but with primers wgkBC_DSM20646_F (GTTAAGTATAAGAAGGA GATATACATATGAGAGAT TATTCGCCATATCCATTA TTAGTAG, SEQ ID NO:7)/wgkBC_DSM20646_R (GGTTTCTTTACCAGACTC GAGTTAT-TTCTCCCTAAA AGGTTTTAACTGTAAGTA TATATC, SEQ ID NO:8). First, vector pRSFDuet-1_6HMBP (discussed previously) was linearized with restriction enzymes BamHI and PstI. The digestion product was then combined with the wgkA PCR fragment by Gibson Assembly, attaching wgkA to the 6HMBP coding sequence in MCS1. The wgkA-containing vector was subsequently treated with NdeI and XhoI to open up MCS2 into which the wgkBC fragment was inserted by Gibson Assembly.

An *E. coli* strain carrying pRSFDuet-1_6HMBPwgkA_wgkBC_DSM20646 and pDB1282 (isc operon), was streaked out from glycerol stock onto an LB agar plate supplemented with Kan (50 mg/ml) and Amp (100 mg/ml) and incubated at 37° C. overnight. A single colony was then used to inoculate a 250-ml flask containing 100 ml LB (plus 50 mg/ml Kan and 100 mg/ml Amp). This seed culture was then used to inoculate 1.6 liter TB in a 4-liter flask or 0.8 liter TB in a 2-liter flask at 1% dilution. Expression cultures were grown continuously at 37° C. with shaking. Arabinose and $FeCl_3$ were added to the culture at an OD600% 0.4 at final concentrations of 0.05% and 0.05 mM, respectively. IPTG was added to the culture at an $OD_{600}$% 0.8 at a final concentration of 0.5 mM. Following 18 h of growth after induction with IPTG, cells were harvested by centrifugation (15,000×g, 30 min, 4° C.) and frozen at 280° C. A typical yield was 5 g cell paste per liter culture.

Cell paste totaling 64 g was thawed and resuspended in NPi-10 (5 ml/g) and supplemented with Benzonase-Nuclease (0.1 ml/ml, Millipore-Sigma), SIGMAFAST Protease Inhibitor Tablet (1 tablet per 100 ml, Millipore-Sigma), and lysozyme (1 mg/ml, Millipore-Sigma). The suspension was stirred for ~45 min and then subjected to three rounds of 4 min of sonication, 15 s on/15 s off, 30% amplitude. During sonication, cells were placed in an ice bath and allowed to rest on ice for several minutes between rounds. Cell debris was removed by centrifugation (33,000×g, 65 min, 4° C.), and the clarified lysate was loaded onto a hand-poured Ni column (1 ml resin per 30 ml lysate), which had been equilibrated with 10 column volumes (CV) of NPi-10. Next, the column was washed with 5 CV of NPi-10 followed by 5 CV of NPi-20. Finally, 6HMBPWgkA was eluted from the column with 10 CV of NPi-500. The elution was then concentrated ~5× using an Amicon Ultra Centrifugal Filter (Millipore-Sigma, Membrane NMWL, 30 kDa) and exchanged into cleavage buffer by gel filtration using Sephadex G-25 resin. The 6HMBPWgkA solution collected off the G-25 column was then supplemented with HRV-3C protease and incubated at 4° C. for 16 h.

The tagless WgkA peptide was purified by preparative HPLC. Following centrifugation and syringe filtration, the reaction mixture was manually injected onto a Phenomenex Jupiter 300-Å C18 column (5 mm, 250×15 mm), which had been equilibrated with 5% MeCN (in water plus 0.1% formic acid). A gradient of 5 to 25% MeCN over 10 min at a flow rate of 12 ml/min was used to elute the peptide, which came off at 21 to 23% MeCN. The relevant fractions were collected and lyophilized.

The lyophilized material was resuspended in ~1 ml cleavage buffer (50 mM Tris-HCl, 150 mM NaCl [pH 8]) and supplemented with $CaCl_2$) at a final concentration of 20 mM and trypsin (2,000 ng per 1 ml). The cleavage reaction was incubated at 37° C. for 16 h and then resolved by HPLC purification using a Phenomenex Luna Omega Polar C18 100-Å (5-mm, 4.6×100 mm) column operating at 0.5 ml/min. An isocratic program of 100% $H_2O$ (plus 0.1% FA) over 15 min was applied to elute tryglysin. A broad peak corresponding to tryglysin was collected from 8 to 10 min. The identity of the purified sample was confirmed by HPLC2Q-TOF-MS.

Example 2—Preparation of Tryglysin B

Preparation of synthetic tryglysin B. *S. mutans* tryglysin was prepared analogously to its *S. ferus* counterpart according to Example 1 with minor modifications. For purification of HRV-3C-cleaved WgkA by preparative HPLC, a gradient of 5 to 35% MeCN over 15 min was used for to elute the peptide which came off at 25 to 27% MeCN. The trypsin reaction was resolved using a Phenomenex Synergi Fusion RP 80 Å (4-mm, 4.6×100 mm) column with a 100% $H_2O$ (plus 0.1% FA) isocratic step. Tryglysin eluted from 5 to 6 min.

Figure 2:
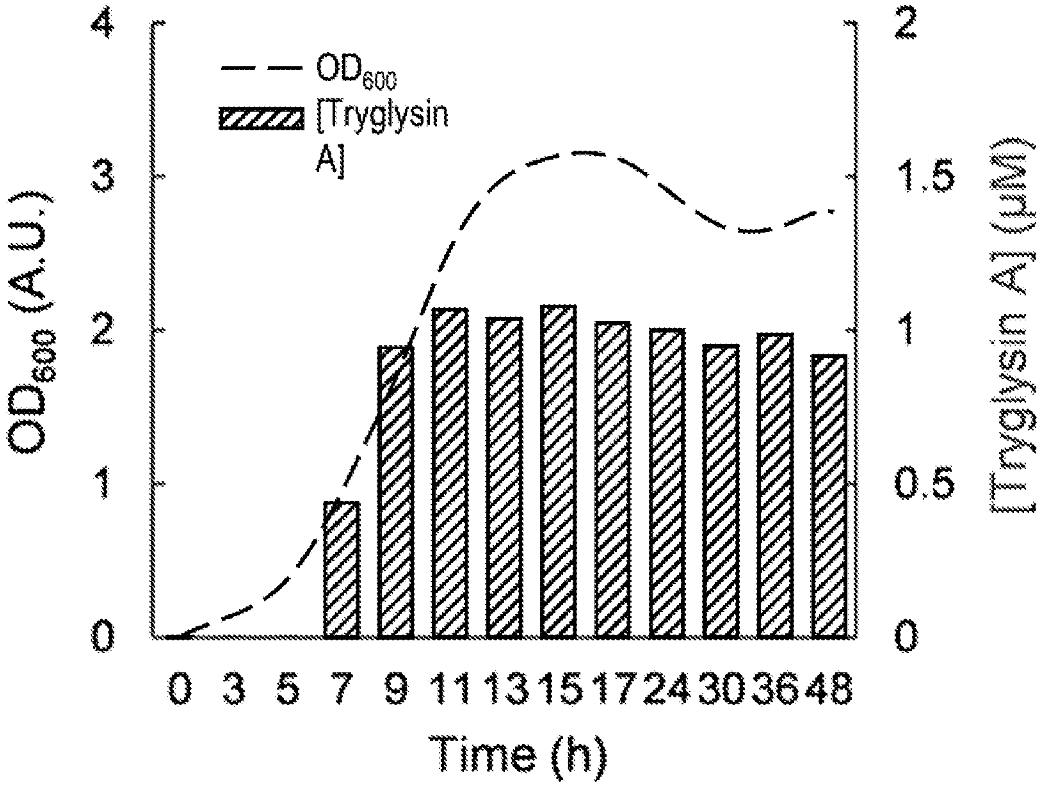
FIG. 2 is a graph showing the quantification of the production of tryglysin A from an embodiment of the present disclosure (hashed bars), where $OD_{600}$ (dashed line) is shown as absorbance units (A.U.).

The synthetic material allows for the quantification of, e.g., tryglysin A production as a function of growth phase. Referring to FIG. 2, the results show that production of tryglysins commences in early stationary phase, peaking at late exponential phase at ~1 mM bulk concentration. Tryglysin A then persists at fairly high titers during stationary phase.

Example 3—Isolation of Tryglysin Directly from *S. ferus*

A tryglysin may be produced using an endogenous producing host, such as *Streptococcus ferus*. Upon growth of the host, tryglysin is expressed, and then the tryglysin is then isolated using a combination of solid-phase extraction (e.g., using solid phase extraction cartridges, such as those available from Waters), and HPLC separation methods.

In one example, *S. ferus* DSM 20646 was grown overnight in Todd-Hewitt broth plus 0.2% yeast extract (5% $CO_2$, 37° C.) to an $OD_{600\sim2}$. Part (11.25 ml) of the overnight culture was centrifuged, and the cell pellet was resuspended in 225 ml of chemically defined media (5% inoculum). After 6 h ($OD_{600\sim0.5}$) 50-ml aliquots were collected every 3 h up to 15 h ($OD_{600\sim2}$). Each aliquot was centrifuged and filtered, and supernatants were passed through a 20-ml Waters Oasis HLB cartridge (Waters). Compounds were eluted from the HLB cartridge with methanol, these methanolic elutions were then evaporated to dryness, and compounds were resuspended in 100 μl of 0.1% Formic Acid (FA) for LC-MS using an Agilent 6540 UHD accurate-mass quadrupole time of—flight (Q-TOF) mass spectrometer with a Phenomenex Luna Omega Polar C18 100-Å (1.6 μm, 150×2.1 mm). Compounds were eluted using an initial 3.5-min isocratic step running 100% $H_2O$ with 0.1% FA, followed by a gradient to 100% acetonitrile (ACN) (plus 0.1% FA) over 16.5 min. The resulting MS data were inspected manually and additionally by using the Find Compounds by Formula feature in the Agilent MassHunter Qualitative Analysis software (version B.06, Agilent) to search for possible tryglysin matches. All ions detected from *S. ferus* extracts that were possible matches to any of the predicted tryglysin mature products based on their accurate mass and isotopic distribution were subsequently targeted for MS/MS analysis. MS/MS spectra from candidate ions were then manually inspected to identify ions with fragment ions consistent with the predicted tryglysin product match. For a time course experiment, *S. ferus* DSM 20646 was cultured as described above with 225 ml of CDM, and 1-ml aliquots were collected at 3, 5, 7, 8, 11, 13, 15, 17, 24, 30, 36, and 48 h. These aliquots were centrifuged, and 3 ml of supernatant were directly injected into the LC-MS using LC-MS using an Agilent 6546 UHD accurate-mass quadrupole time of flight (Q-TOF) mass spectrometer with a Phenomenex Luna Omega Polar C18 100-Å column (1.6 μm, 150×2.1 mm). Tryglysin A was eluted using an initial 2-min isocratic step running 100% $H_2O$ (plus 0.1% FA) followed by a gradient to 50% ACN with 0.1% FA over 4.5 min. Concentrations of tryglysin A in supernatants were calculated from ion counts of tryglysin A $[M+2H]^{2+}$, observed as m z: 412.1957, in samples using a standard curve with synthetic tryglysin A.

Example 4—Growth Inhibition of Streptococcal Pathogens

Growth inhibition of *S. mutans* and *S. ferus* cultures was tested with titrations of both tryglysin A and B over a period of 9 hours.

Figure 3A:
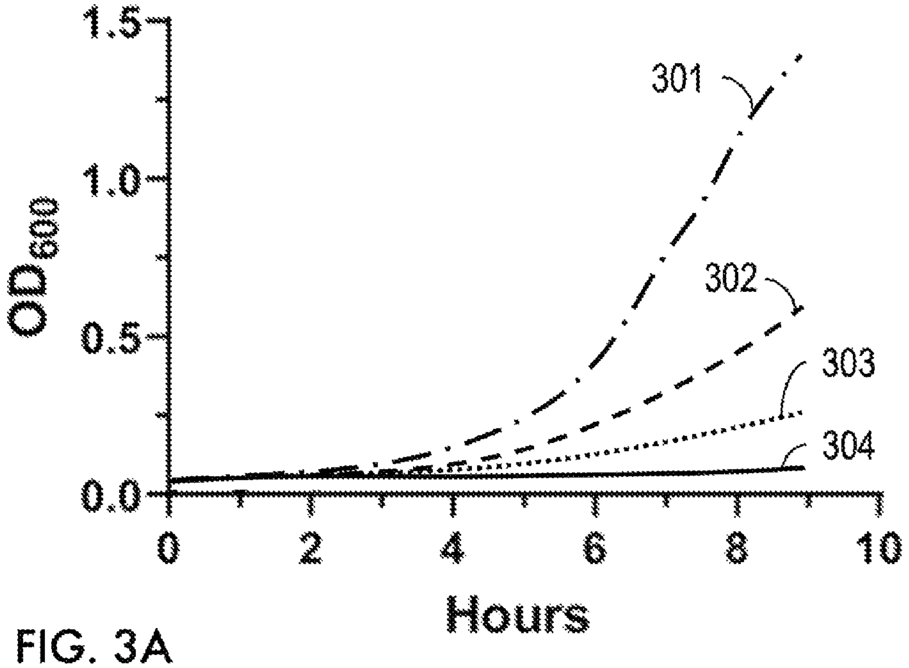
FIG. 3A is a graph illustrating dose-dependent growth inhibition of *S. mutans* by Tryglysin A.

Referring to FIG. 3A, the dose-dependent growth inhibition of *S. mutans* by Triglysin A can be seen. Cultures exposed to no tryglysin A 301, 10 nM tryglysin A 302, 100 nM tryglysin A 303, and 1 μM tryglysin A 304 can be seen. Significant growth inhibition can be seen even at 10 nM concentrations of tryglysin A 302, although further inhibition is seen at higher concentrations (100 nM and 1 μM).

Figure 3B:
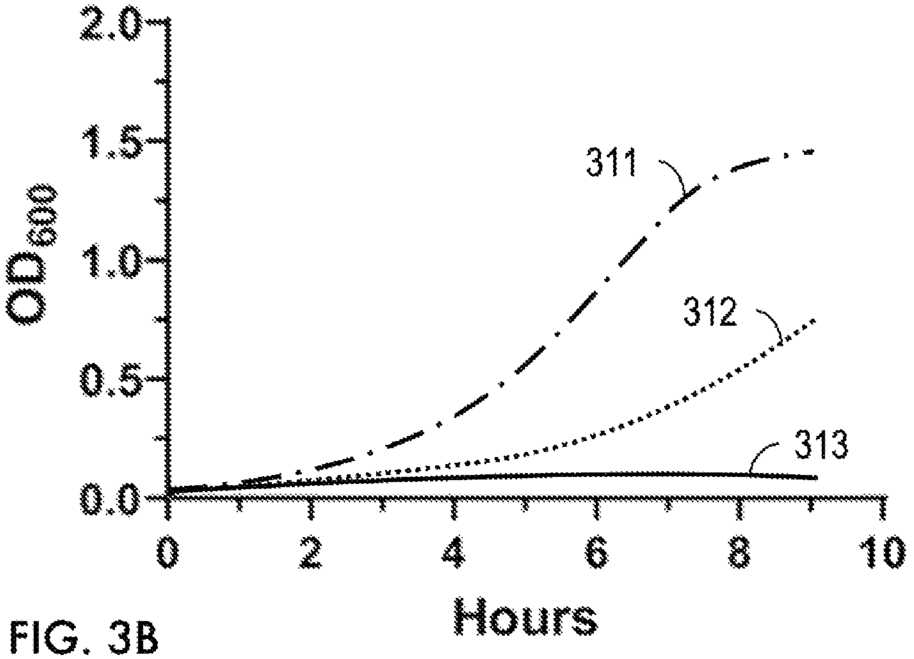
FIG. 3B is a graph illustrating dose-dependent growth inhibition of *S. ferus* by Tryglysin A.

Referring to FIG. 3B, the dose-dependent growth inhibition of *S. ferus* by Triglysin A can be seen. Cultures exposed to no tryglysin A 311, 10 nM tryglysin A 312, and 100 nM tryglysin A 313 can be seen. Significant growth inhibition can be seen at 10 nM concentrations of tryglysin A 312, although complete inhibition can be seen at concentrations of 100 nM or higher.

Figure 3C:
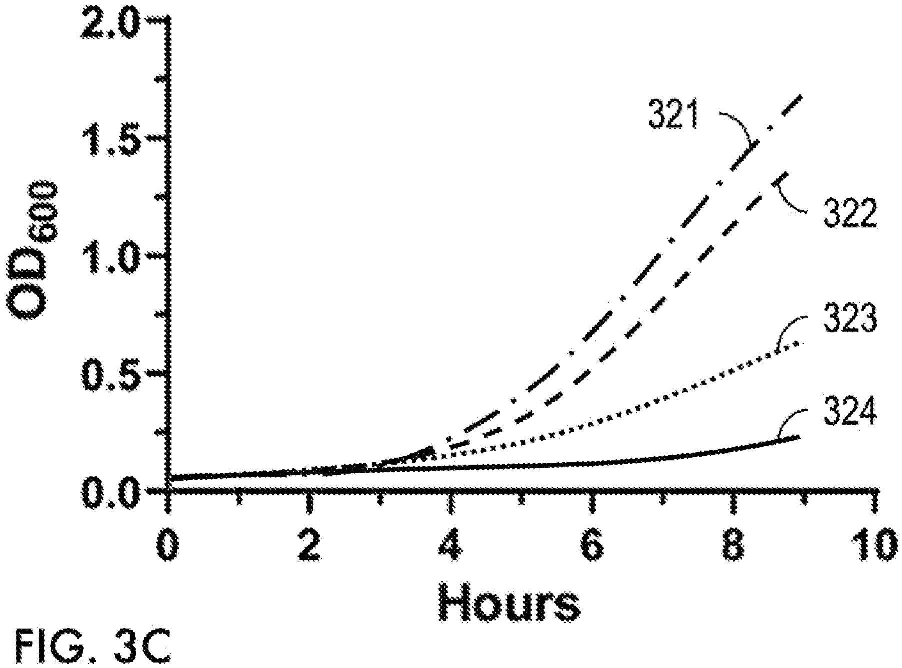
FIG. 3C is a graph illustrating dose-dependent growth inhibition of *S. mutans* by Tryglysin B.

Referring to FIG. 3C, the dose-dependent growth inhibition of *S. mutans* by Triglysin B can be seen. Cultures exposed to no tryglysin B 321, 10 nM tryglysin B 322, 100 nM tryglysin B 323, and 1 μM tryglysin B 324 can be seen. While some inhibition exists at 10 nM, significant growth inhibition will generally require higher concentrations, such as at least 100 nM. In this graph, it is seen that *S. mutans* required 1 μM tryglysin B to be completely inhibited over the 9-h growth assay.

Figure 3D:
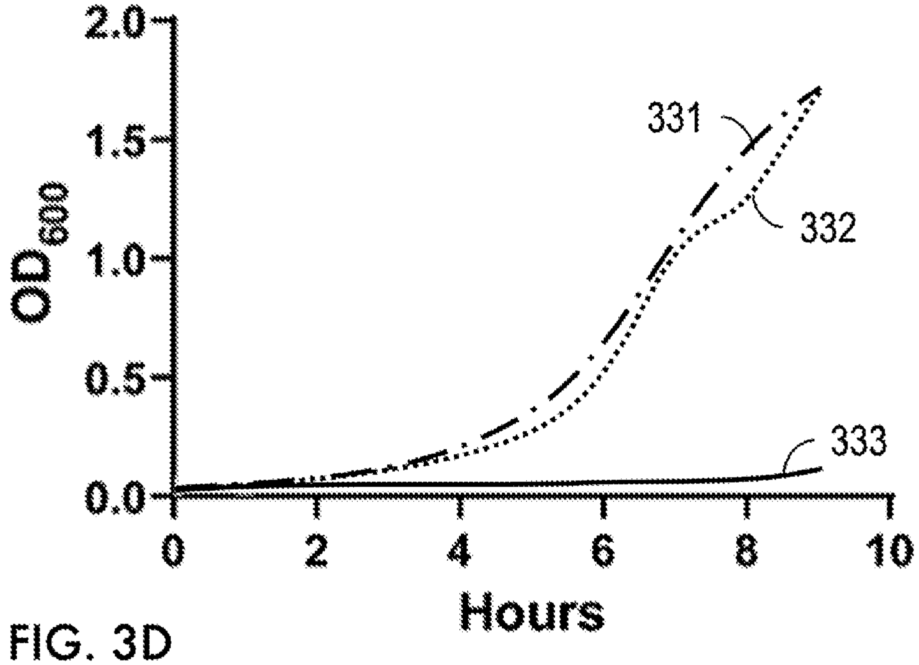
FIG. 3D is a graph illustrating dose-dependent growth inhibition of *S. ferus* by Tryglysin B.

Referring to FIG. 3D, the dose-dependent growth inhibition of *S. ferus* by Triglysin B can be seen. Cultures exposed to no tryglysin B 331, 10 nM tryglysin B 332, and 100 nM tryglysin B 333 can be seen. While minimal inhibition was seen at 10 nM concentrations, compete inhibition was seen at 100 nM concentrations.

Other streptococcal species have similar dose-dependent growth inhibitory responses to tryglysins. WGK peptides inhibit growth of several streptococcal species, but not *E. faecalis* or *L. lactis*. We extended the evaluation of tryglysin inhibitory activity to other bacterial species. Culture growth rates of several Gram-positive species were evaluated upon treatment with 100 nM each antibiotic. Most susceptible to treatments, with complete growth inhibition at only 100 nM tryglysins, were strains of *S. mitis, S. oralis*, and *S. pneumoniae*, each being members of the *mitis* group. Tryglysin A displayed greater inhibitory activity against *S. agalactiae* and to a lower degree, *Streptococcus sanguinis* and *Streptococcus bovis*, than variant B at 100 nM (FIGS. S5A and B and S5E to H). *S. gordonii* displayed an extended lag phase in response to both peptides (FIGS. S5C and D). Unaffected were cultures of *S. pyogenes, Lactococcus lactis*, and *Enterococcus faecalis* (FIG. S4A to F). Thus, for the broad panel of lactic acid bacteria tested, tryglysins displayed a range of specificity for inhibiting streptococcal species but were inert toward *E. faecalis* and *L. lactis*.

Example 5—Morphological Changes Due to Treatment

The impact of tryglysins on gross morphological changes to cell shape was examined at 2, 5, and 7 h after treatment with 100 nM tryglysin A or B by microscopy.

Prestored glycerol stocks of *S. mutans* strains at −80° C. were inoculated into THY broth and incubated overnight at 37° C. in an atmosphere of 5% $CO_2$. CDM was prepared and prewarmed at 37° C. in an atmosphere of 5% $CO_2$ overnight. The next morning, strains were transferred to sterile 15-ml conical tubes and centrifuged at room temperature at 4,000×g for 10 min. Strains were resuspended in 1 ml prewarmed CDM, transferred to microcentrifuge tubes, and centrifuged again at room temperature at 14,000×g for 5 min. Supernatant was discarded, and strains were resuspended in 1 ml fresh prewarmed CDM. Resuspended strains were then inoculated into 6 ml prewarmed CDM at 1:200 dilution. At each time point, strains were monitored by measuring $OD_{600}$ with a GENESYS 30 Vis spectrophotometer (Thermo-Fisher)

If required, at 1 h postinoculation, 100 nM tryglysin A or B was added to the media. For microscopic analysis of samples, 2 ml of live cells was taken at 2 h, 5 h, and 7 h after the addition of tryglysins and examined using an Olympus CKX53 inverted microscope with a 40× LCACHN-iPC infinity objective (LCACHN40XIPC; numerical aperture, 0.55) connected to a SC50 camera (Olympus). Images were processed using Olympus Stream Image Analysis software (Olympus).

Figure 4:
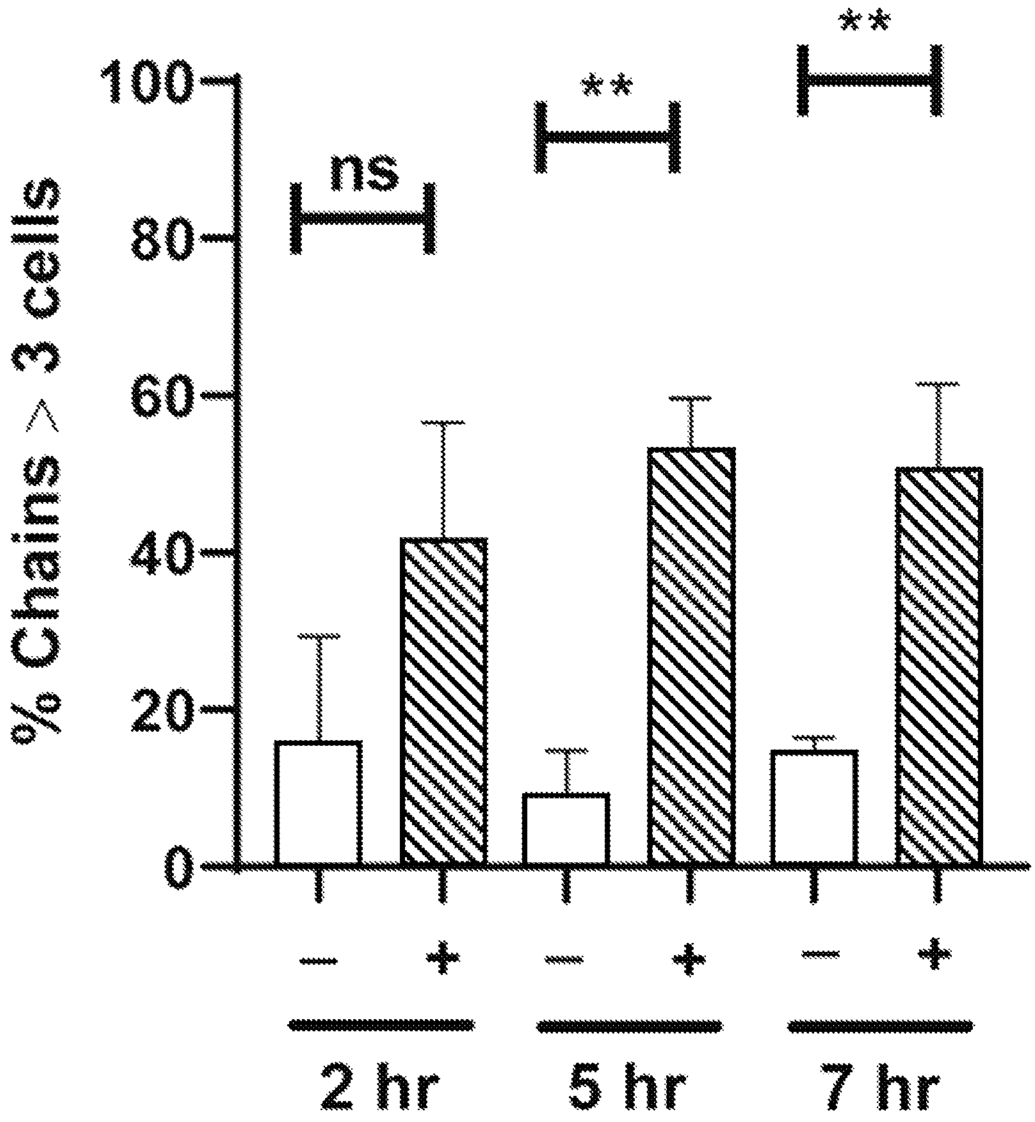
FIG. 4 is a graph showing the quantification of chains greater than three cells in length for *S. mutans* exposed to 100 nM tryglysin A for 2 h, 5 h, or 7 h. A minimum of 100 cells were observed per condition and time point. –, no tryglysin A; +, 100 nM tryglysin A. **, P<0.01; ns, not significant by one-way ANOVA with Dunnet's multiple comparison posttest.

Referring to FIG. 4, it can be seen that relatively fewer chains of cells existed with no treatment (−, white bars), while treatment (+, hashed bars) resulted in the appearance of many long chains of cells, correlating with longer treatment times. At 2 h, small chains were observed; this chaining significantly increased upon tryglysin A addition at 5 h and 7 h and appeared to do the same for tryglysin B-treated cells. The overall effect on morphology is similar with both antibiotic peptides.

Example 6—Inhibition of Other Species

It can also be seen that the disclosed peptides inhibit growth of several streptococcal species, but not others outside of streptococcal species, such as *E. faecalis* or *L. lactis*. Culture growth rates of several Gram-positive species were evaluated upon treatment with 100 nM each antibiotic, and some of the results are shown below in Table 2, where "−" indicates not inhibited; "+" indicates mildly inhibited; and "++" indicates inhibited.

Specifically, bacterial strains were grown from prestored glycerol stocks at −80° C. and inoculated into THY broth. Strains were incubated overnight at 37° C. in an atmosphere of 5% $CO_2$, and the next morning, they were washed and resuspended in fresh, prewarmed CDM as described above in Example 4.

Most susceptible to treatments, with complete growth inhibition at only 100 nM tryglysins, were strains of *S. mitis, S. oralis*, and *S. pneumoniae*, each being members of the *mitis* group. Tryglysin A displayed greater inhibitory activity against *S. agalactiae* and to a lower degree, *S. sanguinis* and *S. bovis*, than variant B at 100 nM. *S. gordonii* displayed an extended lag phase in response to both peptides. Unaffected were cultures of *S. pyogenes, Lactococcus lactis*, and *Enterococcus faecalis*. Thus, for the broad panel of lactic acid bacteria tested, tryglysins displayed a range of specificity for inhibiting streptococcal species but were inert toward *E. faecalis* and *L. lactis*.

TABLE 2

| Species Tested | Inhibition By Tryglysin A | Inhibition By Tryglysin B |
|---|---|---|
| *E. faecalis* V583 | – | – |
| *L. lactis* ATCC 11454 | – | – |
| *S. pyogenes* NZ131 | – | – |
| *S. ferus* DSM 20646 | ++ | ++ |
| *S. mutans* UA159 | ++ | ++ |
| *S. sanguinis* ATCC 10556 | ++ | ++ |
| *S. gordonii* Challis Bt | + | + |
| *S. mitis* CCUG 31611 | ++ | ++ |
| *S. oralis* 108 | ++ | ++ |
| *S. pneumoniae* D39 | ++ | ++ |
| *S. agalactiae* A909 | ++ | + |
| *S. bovis* JB1 | + | + |

Thus, addition of pure tryglysins to *S. mutans* and other streptococcal strains inhibits growth of these organisms and is specific to these strains. This activity is reminiscent of mutacins, and involvement of an Rgg regulator for tryglysin induction is similar to the linkage of MutR to mutacin I, II, and III. However, tryglysins have properties that are distinct from previously identified mutacins. First, although they make use of a RiPP operon for their synthesis, like lantibiotics, they do not possess the characteristic lanthionine and methyllanthionine residues of these bacteriocins. Instead they harbor an unprecedented tetrahydro-[5,6]benzindole motif, which qualifies these tryglysins as a new subclass of RiPPs. Second, the wgk locus appears to be conserved in *S. mutans*, as previous analysis and nucleotide BLAST indicates high levels of conservation of the wgk operon in *S. mutans* strains. This is distinct from mutacins, which vary in their conservation and can be strain specific. Third, and paradoxically, the tryglysins display inhibitory activity toward their producing strains. Typically, streptococcal antimicrobial biosynthetic gene clusters include immunity genes that allow producer strains to be resistant to the natively produced mutacins.

Those skilled in the art will recognize or be able to ascertain using no more than routine experimentation many equivalents to the specific embodiments of the invention described herein. Such equivalents are intended to be encompassed by the following claims.

What is claimed is:

1. A composition comprising a tryglysin for use in treating an infection of at least one streptococcal pathogen, the tryglysin being a macrocyclic compound of formula (I):

(I)

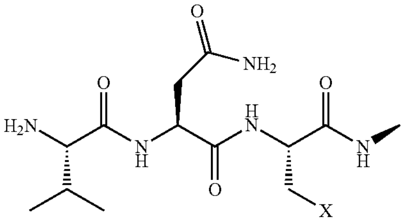

-continued

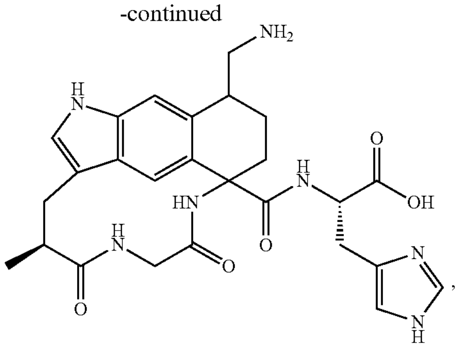

where X is OH or SH.

2. The composition according to claim 1, wherein the at least one streptococcal pathogen is a strain of *S. ferus, S. mitis, S. mutans, S. oralis*, or *S. pneumonia*.

3. The composition according to claim 1, wherein the composition is a pharmaceutical or antibiotic preparation comprising:

the tryglysin; and a pharmaceutically acceptable carrier.

4. The composition according to claim 1, wherein the composition is an oral care composition comprising:

the tryglysin;

an abrasive agent, a flavoring agent, an alcohol, or a combination thereof.

5. A method for treatment or prevention of a disease in a patient caused by at least one streptococcal pathogen comprising:

administering to a patient in need of such treatment or prevention an effective amount of a tryglysin, wherein the tryglysin is a macrocyclic compound of formula (I):

(I)

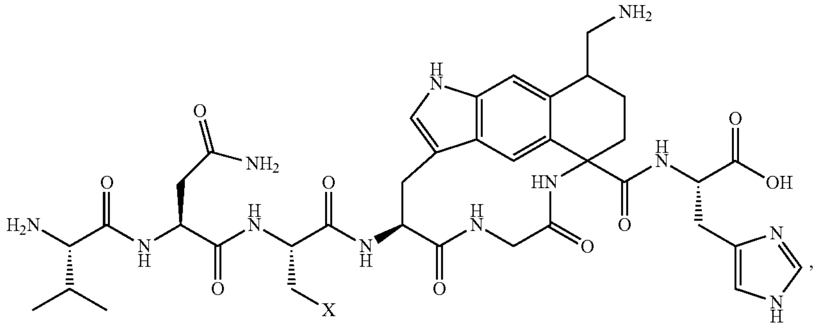

where X is OH or SH.

6. The method according to claim 5, wherein the at least one streptococcal pathogen is a strain of *S. ferus, S. mitis, S. mutans, S. oralis*, or *S. pneumonia*.

7. The method according to claim 5, wherein the concentration of the tryglysin administered is between 10 nM and 500 nM.

8. The method according to claim 5, wherein the minimal inhibitory concentration (MIC) of the tryglysin is <100 nM.

9. The method according to claim 5, wherein an inhibitory effect of the tryglysin is specific to the at least one streptococcal pathogen.

* * * * *

SEQUENCE LISTING

```
<160> NUMBER OF SEQ ID NOS: 8

<210> SEQ ID NO 1
<211> LENGTH: 7
<212> TYPE: PRT
<213> ORGANISM: Streptococcus mutans

<400> SEQUENCE: 1

Val Asn Ser Trp Gly Lys His
1               5


<210> SEQ ID NO 2
<211> LENGTH: 7
<212> TYPE: PRT
<213> ORGANISM: Streptococcus ferus

<400> SEQUENCE: 2

Val Asn Cys Trp Gly Lys His
1               5


<210> SEQ ID NO 3
<211> LENGTH: 21
<212> TYPE: PRT
<213> ORGANISM: Streptococcus mutans

<400> SEQUENCE: 3

Met Leu Thr Lys Lys Glu Phe Ser Val Pro Lys Thr Thr Lys Val Asn
1               5                   10                  15

Cys Trp Gly Lys His
            20


<210> SEQ ID NO 4
<211> LENGTH: 21
<212> TYPE: PRT
<213> ORGANISM: Streptococcus ferus
```

-continued

```
<400> SEQUENCE: 4

Met Leu Thr Lys Lys Glu Phe Ser Val Pro Lys Thr Thr Lys Val Asn
1               5                   10                  15

Ser Trp Gly Lys His
            20


<210> SEQ ID NO 5
<211> LENGTH: 60
<212> TYPE: DNA
<213> ORGANISM: Artificial Sequence
<220> FEATURE:
<223> OTHER INFORMATION: wgkA_DSM20646_F primer

<400> SEQUENCE: 5

agttctgttt cagggtccgg aattcggatc catgtcacct aaaaaagagt ttaatgctcc     60


<210> SEQ ID NO 6
<211> LENGTH: 60
<212> TYPE: DNA
<213> ORGANISM: Artificial Sequence
<220> FEATURE:
<223> OTHER INFORMATION: wgkA_DSM20646_R primer

<400> SEQUENCE: 6

atgcggccgc aagcttgtcg acctgcagtt aatgcttacc ccaactatta actttagttg     60


<210> SEQ ID NO 7
<211> LENGTH: 60
<212> TYPE: DNA
<213> ORGANISM: Artificial Sequence
<220> FEATURE:
<223> OTHER INFORMATION: wgkBC_DSM20646_F primer

<400> SEQUENCE: 7

gttaagtata agaaggagat atacatatga gagattattc gccatatcca ttattagtag     60


<210> SEQ ID NO 8
<211> LENGTH: 60
<212> TYPE: DNA
<213> ORGANISM: Artificial Sequence
<220> FEATURE:
<223> OTHER INFORMATION: wgkBC_DSM20646_R primer

<400> SEQUENCE: 8

ggtttcttta ccagactcga gttatttctc cctaaaaggt tttaactgta agtatatatc     60
```